United States Patent
Fusco et al.

(10) Patent No.: US 8,394,931 B2
(45) Date of Patent: Mar. 12, 2013

(54) ANTI-HMGA1 MONOCLONAL ANTIBODIES, PROCESS FOR THEIR PREPARATION AND THEIR USE FOR THE QUANTITATIVE DETERMINATION OF HMGA1

(75) Inventors: Alfredo Fusco, Naples (IT); Antonio Orlandi, Milan (IT); Maria Luisa Nolli, Milan (IT)

(73) Assignee: Areta International S.R.L., Milan (IT)

( * ) Notice: Subject to any disclaimer, the term of this patent is extended or adjusted under 35 U.S.C. 154(b) by 0 days.

(21) Appl. No.: 12/990,557

(22) PCT Filed: Apr. 29, 2009

(86) PCT No.: PCT/IB2009/005435
§ 371 (c)(1),
(2), (4) Date: Dec. 27, 2010

(87) PCT Pub. No.: WO2009/133452
PCT Pub. Date: Nov. 5, 2009

(65) Prior Publication Data
US 2011/0123557 A1    May 26, 2011

(30) Foreign Application Priority Data
Apr. 30, 2008  (IT) .............................. MI2008A0799

(51) Int. Cl.
*C12P 21/08* (2006.01)
*G01N 33/53* (2006.01)
*G01N 33/574* (2006.01)
(52) U.S. Cl. ............... 530/388.1; 530/388.2; 530/388.8; 530/808; 530/809; 435/7.1; 435/7.21; 435/7.23
(58) Field of Classification Search .................. None
See application file for complete search history.

(56) References Cited

U.S. PATENT DOCUMENTS
2005/0152903 A1 * 7/2005 Newman et al. ........... 424/145.1

OTHER PUBLICATIONS

Scala et al., Adenovirus-mediated suppression of HMGI(Y) protein synthesis as potential therapy of human malignant neoplasias; PNAS, vol. 97, No. 8, pp. 4256-4261, 2000.*
MeSH (HMGA1a Protein, 2002).*
MeSH (HMGA1b Protein, 2002).*
Harlow and Lane (Antibodies, a Laboratory Manual, Cold Spring Harbor Laboratory Press, 1988, pp. 139-243).*
Stratagene Catalog (1988, p. 39).*
International Search Report for PCT/IB2009/005435, mailed Aug. 21, 2009.
Written Opinion of the International Searching Authority for PCT/IB2008/005435, mailed Aug. 21, 2009.
Scala, S. et al., "Adenovirus-Mediated Suppression of HMGI(Y) Protein Synthesis as Potential Therapy of Human Malignant Neoplasias", Proceedings of the National Academy of Sciences of the United States of America, vol. 97, No. 8, (Apr. 11, 2000), pp. 4256-4261.
Schlueter, C. et al., "HMGA1 Proteins in Human Atherosclerotic Plaques", Pathology Research and Practice, vol. 201, No. 2, (Apr. 8, 2005), pp. 101-107.
Hock, R. et al., "HMG Chromosomal Proteins in Development and Diseases", Trends in Cell Biology, vol. 17, No. 2, (Feb. 2007), pp. 72-79.

* cited by examiner

*Primary Examiner* — Peter J Reddig
(74) *Attorney, Agent, or Firm* — Nixon & Vanderhye PC

(57) ABSTRACT

This invention concerns a panel of monoclonal antibodies against the High Mobility Group A 1 protein (HMGA1) and a process for preparing them, as well as the use of said antibodies for the quantitative determination of HMGA1 in biological fluids or in protein Iy sates deriving from lymphocyte cells. This invention also concerns a diagnostic kit for assessing risk factors related to the expression of the HMGA1 proteins.

8 Claims, 1 Drawing Sheet

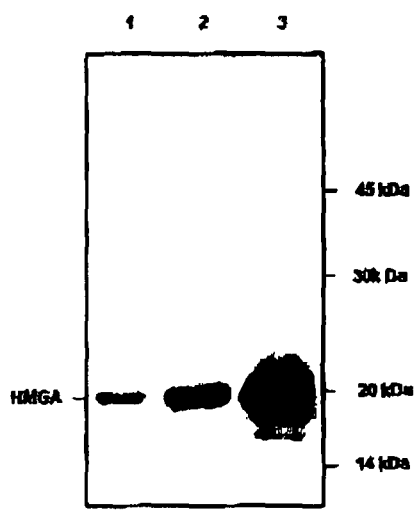
Western Blot analysis of the expression of HMGA1 from cell lysates. Line (1) non transfected HEK293 cells, (2) HEK293 cells transfected with HMGA, (3) recombinant HMGA1 protein.

ANTI-HMGA1 MONOCLONAL ANTIBODIES, PROCESS FOR THEIR PREPARATION AND THEIR USE FOR THE QUANTITATIVE DETERMINATION OF HMGA1

This application is the U.S. national phase of International Application No. PCT/IB2009/005435 filed 29 Apr. 2009, which designated the U.S. and claims priority to IT Application No. MI2008A000799 filed 30 Apr. 2008, the entire contents of each of which are hereby incorporated by reference.

The present invention concerns a panel of monoclonal antibodies against the High Mobility Group A 1 protein (HMGA1) and a process for preparing them, as well as the development of a diagnostic kit for assessing risk factors related to the expression of the HMGA1 proteins.

PRIOR ART

HMGA architectural proteins play an essential role in nuclear biochemical processes which regulate the activation of gene expression in eukaryotes. A possible role of these proteins in regulating the proliferative and differentiative processes is supported by the observation that HMGA proteins would be involved in the pathogenesis of some types of neoplasias in humans. A possible involvement of these proteins in the regulation of the gene expression of the insulin receptor (IR) has recently been described, hypothesising a role thereof in the physiopathology of insulinic action and, therefore, in the transmission of hormonal signals.

Adapted biological and molecular studies have been carried out to understand the exact role that HMGA proteins play in the transmission of the hormonal and proliferative signals in cancer and in some states of insulin-resistance (diabetes mellitus type 2 and obesity) which are often associated with neoplastic diseases. The studies, concerning the regulation of the gene expression of IR by the HMGA proteins, are relevant in the physiopathology understanding of insulin-resistance syndromes and in the other pathological states in individuals with defects of the IR and with anomalies in the transmission of the insulinic signal.

Several experimental evidences indicate that HMGA proteins, abnormally expressed in cancer, could have a role in the functional regulation of the system of the Insulin-like Growth Factor (IGF) (of which IR is one of the components), the alterations of which are frequent in cancer and seem to be important for the development and maintenance of the transformed phenotype.

The explanation of the molecular factors that lead to the non-regulation of the IGF system could be an important aid in the development of new antineoplastic therapies. The identification of tumour markers that cause the alteration of IGF and the understanding of their biological function could be important elements in the diagnosis and treatment of this disease.

The understanding of the molecular role of HMGA proteins in the transmission of proliferative signals could therefore give new suggestions for the preparation of alternative antineoplastic therapies.

The family of HMGA nuclear proteins (High Mobility Group A) is composed of three proteins with a low molecular weight (about 11 kDa) known as HMGA1a, HMGA1b and HMGA2. These proteins are prevalently associated with transcriptionally active chromatin. The proteins HMGA1a and HMGA1b are coded by the same gene, map to chromosome 6p21, and are expressed as a consequence of alternative splicing mechanisms. The proteins HMGA1a and HMGA1b differ for an internal region of 11 amino acids. Instead, the protein HMGA2 is coded by a different gene which in fact maps to chromosome 12q14.3. Although the genes of the proteins HMGA1 and HMGA2 are physically located on different chromosomes, they are nevertheless homologous. HMGA genes are highly expressed during embryo development, vice versa their expression level is decreased in the cells and in completely differentiated tissues.

HMGA proteins are composed of about 100 amino acid residues and are highly homologous with one another. They are characterized by the presence of 3 DNA-binding domains called "AT-hooks". These sites preferentially bind DNA sequences rich in Adenine and Thymine at the level of the minor groove of the double helix. HMGA proteins are often defined as "architectural transcription factors" due to their ability to regulate gene activity through the induction of structural modifications of the DNA and interaction with other nuclear proteins.

In fact, thanks to their intrinsic flexibility, HMGA proteins intervene in specific protein-DNA or protein-protein interactions, inducing both structural changes in chromatin and the formation of stereospecific complexes with a high molecular weight (high-order) called "enhanceosomes" on the promoter/enhancer DNA sequences, regulating the expression of a large number of genes.

Although HMGA proteins are considered important nodes in the network of chromatinic proteins, their role and their physio/pathological implications are not quite clear. For this purpose, animal or cell models have been created in the laboratory, in which the genes that code for these proteins are expressed at higher levels (transgenic mice) or not expressed (knockout).

The experimental cell and/or transgenic animal models shed light on the role of HMGA proteins in neoplastic transformation, for some types of tumour. This observation is so clear that the high concentration of HMGA proteins found can be considered a real marker for neoplastic transformation and of greater susceptibility to metastasis. For example, the increase of the levels of expression of HMGA1 has been suggested as a diagnostic marker of different types of tumour, such as prostate, thyroid, uterine cervix, colon-rectum, pancreas, breast and ovaries tumour. Altogether, these observations effectively give aid to the role of HMGA proteins in neoplastic transformation and in tumour metastatic progression.

The experimental cellular and/or knockout animal models for the HMGA2 protein manifested the mice, with a partial or total deficit of HMGA2, resistance to the induction of obesity by diet, implying a role of the HMGA2 protein in adipocyte proliferation and proposing this gene as a possible target in the treatment of obesity. In fact the "pygmy" knockout mouse presents pathologies of the adipose tissue and phenotypic anomalies characterized by a considerable reduction of its dimensions (about 60% smaller than in wild type mice). The complete or partial absence of this HMGA2 protein causes a reduction of the dimensions of the body associated with a severe deficiency of adipose tissue.

The experimental knockout Animal models for the HMGA1 protein show cardiac hypertrophy associated with type 2 diabetes, indicating a role of HMGA1 proteins in the growth of cardiomyocytes and in the regulation of the glycid metabolism.

It is therefore clear how these proteins, thanks to their structural and functional characteristics, play an important role in the cell, interacting both with the DNA and with other nuclear proteins, influencing numerous physiological processes (growth, proliferation, differentiation, apoptosis) and pathological processes (obesity, tumoral growth and progression).

It is also known that HMGA proteins participate in gene regulation, both inducing conformational variations of cis elements, and interacting directly with other transcription factors, linking neighbouring nuclear factors with one another.

In particular the study of the transcription induction of human INF-BETA following viral infection has shown that two molecules of HMGA1 bind cooperatively the enhancer region of this gene, changing the allosteric conformation of the double strand DNA and thus allowing the housing of NF-kB and of ATF-2/c-Jun. There thus begins the assembly of the enhanceosome, the formation of which is completed through protein-protein interactions between the HMGA1 and the transcription activators. As a result of the assembly of this multiprotein structure, the activation domains of the various transcription factors create a new activation surface that is able to recruit the CREB-binding protein (CBP) and proteins associated with it such as P/CAF and the RNA polymerase II holoenzyme, inducing transcription. Subsequently, the acetylation of HMGA1, mediated by CBP, causes a lowering of the affinity of the HMGA1 for the DNA and consequently the enhanceosome breaking. So the HMGA1 proteins behave as real molecular switches in regulating the gene expression of human INF-beta.

The expression of HMGA1 proteins is transitorily induced during the activation of the lymphocytes or in the inflammatory response, when the genes of the immune system are expressed.

In adult tissues, the expression of the HMGA1 protein is either silent or notably reduced. The involvement of HMGA1 proteins in the regulation of the gene expression of the human insulin receptor has not been completely explained, but it seems that the HMGA1 proteins, by associating with other transcription factors (Sp1 and C/EBP-beta), are able to orchestrate the assembly of a nucleoprotein complex that controls the transcription of the IR gene.

The first stage in the biological action of insulin is its interaction with the insulin receptor (IR), a glycoprotein situated on the cytoplasmic membrane of the target cells, the role of which is essential in the physiopathology of insulin action. Insulin resistance at the level of the peripheral tissues (muscle, liver and fat) is a predominant characteristic in the aetiopathogenesis of diabetes mellitus. Studies carried out on populations with a high prevalence of diabetic disease indicate that insulin resistance (a particular condition in the sugar metabolism which indicates how, to obtain the same metabolic effects, a greater quantity of insulin is needed) precedes the onset of the full-blown diabetic disease, constituting a real predictive marker for this disease. In many diabetic patients the IR is normal and the defect in insulin action is post-receptoral. In other cases (more than 10% of patients with type 2 diabetes mellitus) functional anomalies are present and/or anomalies of expression of the IR due to the presence of specific genetic defects at the level of the codifying region of the IR gene. In many of these cases there are point mutations or deletions which determine the synthesis of an anomalous receptor protein. Instead, in other cases, the gene is normal and the defect is due to anomalies affecting other genes (defects in trans) involved in the functional regulation of the IR gene.

BRIEF DESCRIPTION OF THE DRAWING

FIG. 1 shows Western Blot analysis of the expression of HMGA1 from cell lysates. Lines respectively represent (1) non transfected HEK293 cells, (2) HEK293 cells transfected with HMGA, (3) recombinant HMGA1 protein.

OBJECTS OF THE INVENTION

The object of the present invention is to provide a tool for new therapeutic approaches and/or for the prevention/diagnosis/treatment of insulin resistance in pathologies such as obesity and diabetes mellitus.

The object of the present invention is also to provide a tool for the diagnosis and/or monitoring of neoplastic diseases.

The object of the present invention is further to provide a class of products suited to be used as tools for new therapeutic approaches and/or for the prevention/diagnosis/treatment of insulin resistance in pathologies such as obesity and diabetes mellitus.

A further object of the present invention is to provide a class of products for new therapeutic approaches and/or for the prevention/diagnosis/treatment of insulin resistance as cancer prevention in individuals with protracted hyperinsulinaemia.

The object of the present invention is also a method to restore the physiological levels of HMGA1.

A further object of the present invention is the use of specific expression vectors to restore the physiological levels of HMGA1 in the cells.

Another object of the present invention is to provide a panel of recombinant anti-HMGA1 monoclonal antibodies able to recognise, bind and determine the presence of HMGA1 protein in biological fluids.

Another object of the present invention is the process for selecting recombinant anti-HMGA1 monoclonal antibodies.

Yet another object of the present invention is the process for the production and fermentation of recombinant anti-HMGA1 monoclonal antibodies, as well as the use of a kit for the diagnosis and/or prevention of insulin-resistant pathologies.

These and other objects and further advantages that will be better explained below are achieved through the realisation of a tool and of a class of products suited to be used as tools for new therapeutic approaches and/or for the prevention/diagnosis/treatment of insulin resistance in pathologies such as obesity and diabetes mellitus.

The evidence that HMGA1 proteins are related to the gene that codifies for the human IR and that specific regulating proteins (often organised in the form of a stereospecific multiprotein complex along with other known transcription factors such as Sp1 and C/EBPbeta) include the HMGA1 protein, allows it to assert that the HMGA1 protein, by binding to the promoter region of the IR gene, is able to activate its transcription through the recruiting, at this level of Sp1 and C/EBPbeta.

The functional inhibition of HMGA1 in cells with high levels of IR (IM-9 human lymphoblastoid and HepGw human hepatoma cells) is able to reduce significantly the expression of the receptor on the cytoplasmatic membrane of these cells. On the contrary, the induced expression of HMGA1 in cells with low levels of IR increases the expression of the receptoral protein, demonstrating that the HMGA1 protein plays an important role in the transcriptional activation of the IR gene.

Defects in IR expression have been reported in patients with syndrome of insulin resistance and type 2 diabetes mellitus, in the absence of mutations of the IR gene. In all these cases the receptoral anomalies are almost always followed by anomalies in the transmission of the hormonal signal at the level of the tissues targeted by the insulin action, with consequent alteration of the normal biochemical processes.

These observations allow the hypothesis of the possible pathogenic involvement of the HMGA1 protein in forms of insulin-resistance and type 2 diabetes mellitus in individuals with low IR levels and in the absence of genetic mutations of the IR gene.

This hypothesis is based on observations made on the cells and tissues of some diabetic individuals with low IR levels, in whom the expression of HMGA1 was extremely low and the transactivation of the IR promoter by Sp1 and C/EBPbeta was significantly lower than was observed in the cells and tissues of healthy control subjects.

This invention therefore also concerns the adenoviral construct called Ad-Yas, able to encode antisense sequences of the HMGA1 gene. This virus, which is able to suppress the encoding of HMGA1 proteins, can also lead to the death of various thyroid cell lines (such as ARO and FB-1) derived from anaplastic carcinomas, but not of normal thyroid cells, of either man or rat. Instead, no effect was obtained if the same cells were infected by a control adenoviral construct.

So, according to one of its aspects, the invention concerns the adenoviral construct of the HMGA1 protein.

The cDNA, of HMGA1 with a length of 1,500 base pairs (bp) is inserted after cutting with the restriction enzyme HindIII, to create the sticky ends, in the vector pac-CMVpLpa with sense (s) and antisense (as) orientation to create the following constructs Pac-CMV-HMGA1s pac-CMV-HMGA1as. Both constructs were co-transfected with the adenovirus pJM17 in the cell line Human Embryonic Kidney-293 (HEK-293) (ATCC number: CRL-1573), the fusion of the vectors in the cells generates the definitive construct Ad5CMV-HMGA1(Y)s (Ad-Ys) and Ad5CMV-HMGA1(Y)as (Ad-Yas). The cell line HEK-293 (ATCC) infected with (Ad-Ys) or (Ad-Yas) is lysated 36-40 hours after infection and the viral titre is determined. According to another of its aspects, the invention concerns the recombinant HMGA1 protein. Recombinant HMGA1 may preferably present a tail, or tag, such as histidine or GST or equivalents for purification.

So, according to another of its aspects, the invention concerns the purified HMGA1 protein.

In particular the purified HMGA1 protein was used to immunize BALB/c mice in order to stimulate the production of antibodies against this protein. The immunization of said mice took place in cycles, preferably 3, and through injection, preferably intraperitoneal, in order to obtain a high antibody titre. Said immunized mice were sacrificed so as to take the spleen to use for the cell fusion operation.

Therefore the invention also concerns the hybridomes obtained by fusion of the splenocytes of the immunized mice and of the immortalized cell line, preferably said immortalized cell line is tumoral, preferably said immortalized cell line is murine, more preferably said murine line is of myeloma that does not secrete immunoglobulins, even more preferably said murine line of non-secreting myeloma is for example NSO (murine myeloma line of BALB/c mouse not secreting immunoglobulins). Preferably the operation of fusion of the splenocytes and of the murine cell line takes place in the presence of PEG1500. In particular the spleen of said immunized mice, after the homogenization, is fused with said myeloma cells and placed in suitable culture conditions.

Said suitable culture conditions consist, for example, of the use for expansion of said hybridomes of a suitable culture medium, for example DMEM and more preferably DMEM medium with the addition of HAT and Hybridimax, and even more preferably said DMEM with additions contains at least 10% HAT and 2% Hybridimax with respect to the total volume of the medium.

The hybridomes generated as described above produce mAb (monoclonal antibodies) against the HMGA1 protein. In order to obtain mAb with a high affinity of recognition and binding for the HMGA1 protein, the cells of the hybridomes were placed in limiting growth conditions through plating in multiwell plates. Said plating operation generates for each well a clone line that specifically expresses only one type of antibody against HMGA1.

So according to another of its aspects, this invention also concerns the process of expansion and selection of the clone population and of the individual closes, as well as the process for purifying the recombinant anti-HMGA1 antibodies.

Preferably the expansion method consists of plating, growing and collecting said hybridomes in special multiwell plates.

A further aspect of the present invention is the selection and identification of the cell clones generated by said expansion method. Preferably said selection and identification are accomplished in two successive steps, primary and secondary, by means of indirect ELISA and isotypical analysis. 40 clones are therefore identified as positive from the primary step and 32 clones from the secondary step. After stabilisation, according to said culture method, 20 clones are chosen, listed in Table 1, from the group of 32, in particular 15, and specifically 4, and among these one in particular identified as either 2G16 or 21G6 (so in this text the terms 2G16 and 21G6 refer to exactly the same clone). The date of deposit was Mar. 18, 2008. The accession number for the deposit is PD 08001. The deposit material are cell clones. The name and address of the depository is Autoritá Internazionale di Deposito, AID Genova; Largo Rosanna Benzi, 10-16132, Genova-Italy.

TABLE 1

| Stabilised clones |
| --- |
| 2E3 |
| 3E7 |
| 6F4 |
| 8G6 |
| 12B3 |
| 15F4 |
| 16C10 |
| 16B10 |
| 16G10 |
| 18C6 |
| 19C7 |
| 21F7 |
| 21G6 |
| 22E2 |
| 23H3 |
| 25G1 |
| 26E8 |
| 27B9 |
| 28C8 |
| 29D8 |

Another object of the present invention is the clone subpopulation generated by said preferred clone 2G16 (PD 08001), according to said methods of culture, expansion, selection and identification methods described above, and preferably the clone 2G16/18 also identified as 21G6/18 (so in this text the terms 2G16/18 and 21G6/18 refer to exactly the same clone. The deposit date was Mar. 18, 2008. The accession number is PD 08002. The deposited material are cell clones. The name and address of the depository is Autoritá Internazionale di Deposito, AID Genova; Largo Rosanna Benzi, 10-16132, Genova-ITALY. In particular a further object of the invention is the antibody panel generated by said cell clones, that is the monoclonal antibodies generated by every single selected clone and directed against the HMGA1 protein through the purification process. Said purification process is carried out by chromatography, more preferably by affinity chromatography and even more preferably by affinity chromatography on a HiTrap-Proteina G column (General Electric).

In particular a further object of the invention is the antibody panel generated by said cell clones, that is the monoclonal antibodies generated by every single selected clone and directed against the HMGA1 protein through the purification process. Said purification process is carried out by chromatography, more preferably by affinity chromatography and even more preferably by affinity chromatography on a HiTrap-Proteina G column (General Electric).

The anti-HMGA1 mAbs produced according to the invention are of the type IgG. The evaluation of the isotype is preferably carried out according to the instructions of the ISOTRIP kit.

A further object is the method of industrial production of said mAbs against the HMGA1 protein, preferably said production method is carried out in bioreactors and more preferably in miniPerm/Viva Science Sartorius bioreactors with a cut-off of 12.5 Kda. In particular any clone cell chosen from the panel, according what is above described, is inoculated and made to grow in a volume of culture medium containing serum-free medium (SFM) and complete medium for hybridomes, preferably with a 75% concentration of SFM and 25% of complete medium for hybridomes.

A further object of the invention is the purification of the mAbs against the HMGA1 protein by chromatography as described above.

Another object of the present invention is the quantitative determination of HMGA1 in the biological fluids using any one of the mAbs from the clone panel described above, preferably the determination is carried out with purified mAb 2G16/18. Said mAb 2G16/18, obtained according to the process described above, was further characterized by SDS-PAGE in both native and reducing conditions, and with WESTERN BLOT analysis (WB). The molecular weight is that of class IgG, that is about 150 Kd, and the WB demonstrated that the antibody chosen is specific for HMGA1. Preferably the determination of the quantity of HMGA1 in the biological fluids is carried out with ELISA of a competitive type.

The purified antibody 21G6/18 was used for the preparation of the assay for determining the HMGA1 in the biological fluids. The assay is a competitive ELISA based on the competition of the bond between HMGA1 in the solid phase and HMGA1 in solution, in the presence of a specific antibody for the antigen. The quantitative determination of the HMGA1 concentration is carried out titrating the samples against a standard line obtained using the purified HMGA1 protein. The first assays were carried out to determine the quantity of HMGA1 to be used for coating the multiwell plates and the standard curve of antibody. Different protein concentrations were dispensed onto the microtiters plate with different antibody concentrations, establishing that the optimal concentration of HMGA1 to be used for the coating is 0.5 µg/ml (0.05 ml/well) while the optimal antibody concentration is 0.002 µg/ml. To optimize the best dilution of the secondary antibody linked to peroxidase, 4 concentrations of the standard antibody were tested, varying the dilutions of the secondary antibody. The chosen dilution was 1:2000.

In order to assess the reproducibility and accuracy of the assay and of the results, investigations were also carried out on the equivalence of the matrices, testing the effect of the addition of 10% and 20% of serum to the dilution buffer of the antibody standard curve, preferably the suitable condition is 10%.

In order to define the sensitivity of the assay, the standard curve of HMGA1 was determined by incubating any one of the mAbs, for example 21G6/18, with variable concentrations of HMGA1 protein between 10 µg/ml and 0.001 µg/ml. The response dose curve was obtained in the interval of 0.01-0.1 µg/ml of HMGA1. The sensitivity of the assay is such as to allow the quantitative determination of HMGA1 in the biological fluids or in the protein lysates deriving from lymphocyte cells.

Preferably each assay contemplates the simultaneous analysis of:
standard competition curve obtained with purified HMGA1 at different concentrations (8-2-0.5-0.125-0.031-0.0078-0.002-0 µg/ml with double/triple-blind assessments).
analysis samples assessed not diluted and in dilution 1:2.
analysis samples with the addition of a spike, where spike means a known quantity of analyte added to a solution to demonstrate the completeness of recovery.

For the determination of the numeral value for quantifying biological fluids, analyses were made to calculate the following:
mean of the competition percentages of standard lines
logarithm of the relative concentration
linear regression by interpolation
slope and $r^2$.

The assay is reliable for values of $r^2$ between $0.96<r^2<1$ and for analysed samples that show a recovery of a spike of HMGA1 with a variation of less than 25% of the expected known value. The assay allows a line to be obtained for calculating the concentration of HMGA1 present in the samples to be analysed, for example samples of biological fluids that may be examined, for example components of said fluids, such as for example the lymphocyte component. The assay for the determination of HMGA1 presents a sensitivity with a measuring limit of about 0.035 µg/ml.

A further object of the present invention is a process for ascertaining, by assay, the relation between the levels in terms of concentration of the HMGA1 protein in the biological fluids or in the protein lysates deriving from lymphocyte cells.

The invention also concerns a process for ascertaining, by assay, the existence (or predisposition) of some pathologies closely connected with insulin resistance, such as diabetes mellitus type 2 and obesity. In particular, the assay allows the determination of the relation between low levels of HMGA1 protein and the predisposition for the development (or the full-blown presence) of insulin-resistant pathologies, which have a considerable social and medical impact. In the case of the results given in table 2, the values for healthy subjects are in a concentration interval ranging from 7.5 to 18.7 µg/ml (mean±mes 11.51±0.79, n=15) while for insulin-resistant subjects the same values are in a concentration interval ranging from 2.9 to 7.5 µg/ml (mean±mes 5.92±0.31, n=17) (P<0.0001).

The invention also concerns the use of constructs and recombinant anti-HMGA1 monoclonal antibodies.

The objects of this invention also include a kit for the prevention/diagnosis/treatment of pathologies related to insulin resistance such as obesity and diabetes mellitus.

On the basis of the above description, the invention is composed of the following aspects and objects:
Construction of a recombinant adenoviral construct that encodes sense and antisense sequences of the gene that codifies for the HMGA1 protein Infection of the cell line HEK-293 with the generated adenoviral construct Purification of the recombinant HMGA1 protein from the cells HEK-293

Inoculation and immunization of the purified recombinant HMGA1 protein in BALB/c mice Removal of the spleen from the sacrificed immunized mice Production of hybridomes through fusion of the splenocytes taken with tumoral cells, preferably of myeloma not secreting immunoglobulins Expansion of the pool of hybrid cells in suitable growth and culture conditions, that is through plating in multiwell plates Primary selection (first screening) of the clone panel obtained by ELISA to identify the best clones Identification of the best clones and further selection process in limiting growth conditions, secondary selection (second screening)

Evaluation of the isotype

Purification of the anti-HMGA1 mAbs by chromatography

Production in bioreactor and subsequent purification of the anti-HMGA1 mAbs by chromatography Assay for determining the quantity of HMGA1 in the biological fluids or in the protein lysates deriving from lymphocyte cells, through the use of the mAbs obtained as described in the previous points Process to assess the relation between the levels in terms of concentration of the HMGA1 protein in the biological fluids and in the protein lysates deriving from lymphocyte cells and the presence or any predisposition for pathologies related to insulin resistance, such diabetes mellitus or obesity Kit for the prevention/diagnosis/treatment of pathologies related to insulin resistance such as obesity, diabetes mellitus.

EXPERIMENTAL PART

Example 1

Preparation of the Recombinant Adenoviral Construct

The cDNA of the HMGA1 gene, with a length of 1,500 base pairs, was inserted with sense (s) and antisense (as) orientation in a vector pac-CMVpLpa, exploiting the sticky ends after cutting with the restriction enzyme HindIII, to generate a recombinant construct pac-CMV-HMGA1s and pac-CMV-HMGA1as. The vectors obtained and the adenovirus pJM17 were co-transfected in the human embryonic kidney cell line HEK293 (ATCC) to generate the recombinant viral, constructs Ad5CMV-HMGI (Y)s (Ad-Ys) and Ad5CMV-HMGA1 (Ad-Yas). The virus stocks were expanded in HEK293 cells, after having been collected 36-40 hours after injection and lysated. The viral titre was determined, assessing the plaque-forming units (pfu) in HEK293 cells. The vector AdCMV-lacZ (Ad-lacZ) (Quantum Biotechnology) was used as a control.

Generation of the Recombinant HMGA1 Protein

The cDNA of HMGA1b was cloned in the plasmid pET2c/His. Cells of *E. Coli*, strain BL21, were transformed with the expression vector pET2c/His-Hmga1b and grown in LB. The expression of proteins was induced by adding 200 µl of Iso-propyl-β-D-thiogalactopyranoside (IPTG) 1M (Promega). The bacteria were resuspended in 20 ml of cold PBS (140 mM NaCl, 20 mM sodium phosphate pH 7.4) with the addition of phenylmethylsulphonyl fluoride (PMSF), protease inhibitors (Roche) and Triton X-100 in final concentration 1%. Bacterial lysis was carried out using the French Press. Nickel sulphate activated resin was added to the supernatants of the lysated samples. Elution was carried out with a solution composed of imidazol in final concentration 500 mM in PBS.

Immunization of BALB/c Mice

The purified recombinant HMGA1 protein was used to immunize 3 female BALB/c mice 7 weeks old. The mice were injected with 50 µg of the protein in incomplete Freund's adjuvant via intra-peritoneal route 60 days prior to fusion. The same operation was performed in the same conditions 30 days later. The antibody titre in the mouse serum was determined by indirect ELISA from samples taken from the tail of the treated animals. A further injection of 50 µg of the protein was performed on the animals that showed an antibody titre higher than 1:10,000 three days prior to fusion.

Production of Hybridomes and First Limiting Dilution (LD)

At the end of 60 days of immunization the mice were sacrificed, the spleen was taken from each animal in sterile conditions and divided into two parts for the formation of hybridomes and for freezing. The spleen portion to be frozen is kept in FCS (90%) and DMSO (dimethyl sulfoxide) 10%.

Part of the spleen was homogenated by mechanical disaggregation and treated as follows:
 first wash in 5 ml of DMEM medium
 second wash in 30-40 ml of DMEM medium
 fusion of the splenocytes with the NSO murine cell line of myeloma of mouse not secreting immunoglobulins. A quantity of a $5 \times 10^7$ NSO cells was suspended in 20 ml of medium (about 1 NSO cell to 5 splenocytes) with the addition of PEG 1500.
 hybrodomes resuspended in DMEM with the addition of 10% HAT, 2% Hybridimax
 seeding of the hybridomes in 10 plates with 96 wells Primary Screening, First LD Indirect ELISA was carried out on the clone population to identify the positive clones, that is those which produce recombinant monoclonal antibodies against the protein HMGA1-GST.

Plates with 96 wells (Hysorb NUNC) were coated with a solution of HMGA1 in a concentration of 1 mg/ml in PBS 1× at pH 7.2. A volume of 50 µl of solution was distributed in each well with an incubation time of about 12 hours at 4° C.

The plates thus manipulated were washed 3-4 times in PBS-Tween20 0.05% and then saturated in PBS-BSA 3% for 1 hour at room temperature. This operation allows the avoidance of aspecific bonds.

The content was emptied from the plates and a volume of 50 µl/well of supernatant of the hybridomes was added for an incubation time of 1 h and 30 minutes at room temperature.

The plates were then washed and incubated with a dilution of 1:1000 of a peroxidase-conjugated goat-anti-mouse antibody for 1 hour at room temperature. After 3-4 washes the plates were incubated with 200 µl/well of a solution of OPD (O-Phenylenediamine) 1 mg/ml in citrate buffer pH 5, 1.7 mM $H_2O_2$. The development of colour is observed at the optical density of 490 nm with respect to the control conditions (without antigen and without antibody).

40 positive clones were identified and among these the clone 21G6 (PD 08001) was preferred.

Secondary Screening, Second LD

The 40 positive clones which produce specific recombinant antibodies that recognise HMGA1 were further selected with the LD method. The clones were seeded at a cell density of 30 cells/plate (in plates with 96 wells) and with triple sampling of three plates/clone.

The limiting growth conditions allow monoclonal cell lines to be obtained which produce specific antibodies for the antigen. As illustrated by table 1 for primary selection, of the selected 40 and 32 clones respectively, and after stabilisation in culture of 20 clones, the clone preferred is 2G16/18 (PD 08002).

Clone Classification by Isotype

Determination of the Isotype of the Recombinant Anti-HGMA1 Monoclonal Antibodies The subclass of immunoglobulins was determined using the Isostrip kit. The supernatant to be tested was diluted 1/10 in PBS and 150 ul were dispensed in the test-tube containing the freeze-dried beads coated with direct antibodies against the light chains of murine immunoglobulins. The strip on which the specific anti-mouse antibodies are immobilised was inserted in the test-tube containing the resuspended reagent. According to the indications supplied by the kit manufacturer, after the appearance of the control lane the presence of the characteristic lane of the specific antibody class was observed, that is IgG.

SDS-PAGE and Western Blot

The accuracy of the molecular weight of the antibodies produced is assessed, loading said mAb in a Laemli buffer, together with suitable controls, on prepacked acrylamide gel (PhastGel, GE) with a homogeneous density (20% polyacrylamide) and gradient (4-15% or 8-25% of polyacrylamide). Electrophoresis is carried out with the electrophoretic system (PhastSystem, GE), at 15° C., using the buffers for SDS_PAGE (SDS-Buffer Strips, GE). A separate gel, as indicated in FIG. 1, is prepared for then transferring the samples onto nitrocellulose. The transfer was carried out with the transfer appliance (GE) and an ELISA was performed on the nitrocellulose membrane, after transferring, incubating with a secondary peroxidase-conjugated antimouse antibody IgG (Sigma) and then revealing the complex with N,N dimethyl formamide.

Example 2

Production of Monoclonal Antibodies in a miniPERM Bioreactor

The selected production of monoclonal antibodies was carried out after adaptation in SMF (Serum Free Medium) in a miniPERM bioreactor. This single-use cylindrical bioreactor comprised a culture chamber (volume 30 ml) where the cells are inoculated and a plastic vessel (volume 350 ml) fitted on the culture chamber into which the medium for nourishing the cells is placed. The chamber and the vessel are separated by an ultrafiltering membrane which allows only the nutrients to pass into the culture chamber and prevents the antibody being spread into the vessel and diluted. The bioreactor is placed on a rotating roller in the incubator at 37° C., 5% CO2. The method allows very concentrated volumes of antibodies to be obtained.

Example 3

Purification by Chromatography

The purification of the class IgG antibodies is carried out by affinity chromatography on HiTrap-Protein G (General Electric). The column is regenerated with phosphate buffer 20 mM pH 7.4 and re-balanced with phosphate buffer pH 8, the initial sample containing the antibody is loaded on the column. After washing with the same buffer, the antibodies are eluted with a glycine buffer (glycine 0.1 M in bidistilled water, pH 2.7) and then concentrated with precipitation in ammonium sulphate at 70% saturation and subsequent dialysis against PBS using a membrane with 6-8000 Da cut-off (Millipore). The dialysed sample is dosed with protein dosage (Biorad) by spectrophotometer, the reading is taken at 280 nm.

SDS-PAGE and Western Blot

To check the correctness of the molecular weight of the produced antibodies, they are loaded in a Laemli buffer, together with suitable controls, on prepacked acrylamide gel (PhastGel, GE) with a homogeneous density (20% polyacrylamide) and gradient (4-15% or 8-25% of polyacrylamide). Electrophoresis is carried out with the electrophoretic system (PhastSystem, GE), at 15° C., using the buffers for SDS_PAGE (SOS-Buffer Strips, GE). A separate gel is prepared for transferring the samples onto nitrocellulose. The transfer was carried out with the transfer appliance (GE) and an ELISA was performed on the nitrocellulose membrane, after transfer, incubating with a secondary peroxidase-conjugated antimouse antibody IgG (Sigma) and then revealing the complex with N—N dimethyl formamide Adaptation to Serum-Free Medium and Production Kinetic The selected cell clones were then seeded on a plate of 24 wells at a concentration of $1 \times 10^4$ cells/cm$^2$ in quadruple repetition, in a plate of 24 wells, placing them, once they arrived at the confluence, in an increasingly stronger concentration of Serum-Free Medium (SFM) (0%, 25%, 50%, 75%, 100%) in complete medium for hybridomes. The adaptation of the cells was evaluated as cell viability and production of recombinant anti-HMGA1 monoclonal antibodies. The adapted cells were subjected to a production kinetic in a flask for 6 days, at the same time controlling the following parameters: viability, glucose consumption, lactate production, production of anti-HMGA1 antibodies.

Example 4

Production in a Bioreactor

The selected cell clones were counted and coloured with Tripan Blue to have a viability of at least 80%. $5.5 \times 10^7$ cells were inoculated in a volume of culture medium containing 75% SFM and 25% complete medium for hybridomes. The inoculation was carried out by sterile syringes in a miniPERM/Vivascience Sartorius production module with a cut-off of 12.5 Kda. The module was mounted on the feeding module and the entire bioreactor was stirred on a rotating support in a CO$_2$ incubator. Samples were taken to check viability, production and metabolic parameters using sterile syringes under laminar flow hoods in the production module. At the end of the production process the antibody, in a volume of about 35 ml, was taken from the production module along with the cells from which it was then separated by centrifugation. The antibody was purified by affinity chromatography on HiTrap-Protein G (General Electric), according to the method described in example 3.

Competitive ELISA to Determine the HMGA1 in Biological Fluids

Plate with 96 wells for ELISA (Maxisorp—NUNC) were incubated with a solution of HMGA-his in PBS pH 7.3, 0.05 ml/well (1 µg/ml) for about 12 hours at 4° C. After incubation the plates were washed by means of a process of emptying and filling with PBS, then blocked with 0.1 ml/well with a solution of BSA in PBS for 2 hours at room temperature.

The plates were emptied without washing. To the plates were added 0.05 ml/well of a solution of the following components previously incubated for 2 hours at room temperature in PBS, 0.3% BSA, 0.05% Tween 20. Different experimental conditions were tested:
1) decreasing concentrations of anti-HMGA1 antibody (from 1 µg/ml to 0.001 µg/ml) with a fixed quantity of HMGA1

2) fixed concentration of anti-HMGA1 antibody and decreasing concentrations of HMGA1 or biological samples containing HMGA1
3) conditions as in points 1 and 2 on control cells, then decreasing concentrations of anti-HMGA1 antibody and/or of buffer alone.

The plates were incubated for 2 hours at room temperature and then washed with PBS-Tween 0.05%.

To the plates were added 0.05 ml/well of the secondary peroxidase-conjugated antimouse antibody Igs F(ab')2 diluted 1:1000 in PBS-Tween 0.05% and left in incubation for 1 and a half hours at room temperature. The plates were washed with PBS-Tween 0.05% and were added 0.15 ml of chromogenic substrate thereto (1 g/L of o-phenylendiamine (OPD) and 3.5 mmol/L of hydrogen peroxide in 0.1 M sodium citrate buffer, pH 5). Colour development was stopped after about half an hour by adding 0.05 ml/well of sulphuric acid 4.5 M and the absorbance was measured after 10 minutes at 492 nm with the TEKSCAN. The standard curve was obtained by plotting, that is converting the logit (logarithmic) transformation of the absorbance (the maximum absorbance at 1 mg/L) as a function of the mAb concentration.

Quantitative Determination of HMGA1

The purified antibody 21G6/18 was used for the preparation of the assay for determining the HMGA1 in the biological fluids. The assay is a competitive ELISA based on the competition of the bond between HMGA1 in the solid phase and HMGA1 in solution, in the presence of a specific antibody for the antigen. The quantitative determination of the HMGA1 concentration is carried out titrating the samples against a standard line obtained using the purified HMGA1 protein. The first assays were carried out to determine the quantity of HMGA1 to be used for coating the multiwell plates and the standard curve of antibody. Different protein concentrations were dispensed onto the microtiters plate with different antibody concentrations, establishing that the optimal concentration of HMGA1, to be used for the coating, is 0.5 ug/ml (0.05 ml/well) while the optimal antibody concentration is 0.002 ug/ml. To optimize the best dilution of the secondary antibody linked to peroxidase, 4 concentrations of the standard antibody were tested, varying the dilutions of the secondary antibody. The dilution chosen was 1:2000.

In order to ensure the reproducibility and accuracy of the assay and of the results, investigations were also carried out on the equivalence of the matrices, testing the effect of the addition of 10% and 20% of serum to the dilution buffer of the antibody standard curve. The optimal condition was 10%.

Once the best antibody concentration to use had been determined, to define the sensitivity of the assay, the standard curve of HMGA1 was determined by incubating the antibody with variable concentrations of protein between 10 µg/ml and 0.001 µg/ml. The response dose curve was obtained in the interval of 0.01-0.1 µg/ml of HMGA1. The sensitivity of the assay is such as to allow the quantitative determination of HMGA1 in the biological fluids or in the protein lysates deriving from lymphocyte cells. Each assay contemplates the simultaneous analysis of:

standard competition curve obtained with purified HMGA1 at different concentrations (8-2-0.5-0.125-0.031-0.0078-0.002-0) µg/ml with double/triple-blind assessments.

analysis samples assessed not diluted and in dilution 1:2.

analysis samples with the addition of a spike

The mean of the competition percentages of standard lines and the logarithm of the relative concentration were calculated. The intercept, slope and $r^2$ parameters were calculated with the linear regression function. The assay must be repeated in the case of a value $r^2 < 0.96$ and/or if the sample containing the HMGA1 spike deviates from the expected value by >25%. From the line thus obtained it is possible to calculate the concentration of HMGA1 present in the samples to be analysed. The assay thus prepared shows a detection limit of 0.035 µg/ml.

The results of the competitive ELISA for determining the HGMA1 in the serum of biological samples are shown in Table 2.

In particular in Tab. 2 with series 1 and series 2 the samples of different subjects dosed at different times. In particular, in series 1 the samples 1, 2, 4, 5, 6, 7, 8, 10, 11 represent the healthy control subjects, the remaining samples listed represent probably insulin-resistant or diabetic subjects. In particular, in series 2 the samples 1, 2, 3, 4, 5, 6 represent the healthy control subjects, the remaining samples listed represent probably insulin-resistant or diabetic subjects. The values indicated in µg/ml refer to the concentrations of HMGA1 protein in the sample.

TABLE 2

Determination of HMGA1 in biological samples
TITRATION OF HMGA1 IN SERUM
SAMPLES BY COMPETITIVE ELISA

| Series 1 | | Series 2 | |
|---|---|---|---|
| sample number | HMGA1 µg/ml | sample number | HMGA1 µg/ml |
| 1 | 10.3 | 1 | 11.7 |
| 2 | 11.9 | 2 | 7.5 |
| 4 | 10.1 | 3 | 9.7 |
| 5 | 15.4 | 4 | 12.8 |
| 6 | 11.6 | 5 | 8.1 |
| 7 | 12.4 | 6 | 7.8 |
| 8 | 14.8 | 7 | 7.0 |
| 10 | 18.7 | 8 | 5.2 |
| 11 | 9.9 | 9 | 2.9 |
| 12 | 6.6 | 10 | 4.2 |
| 13 | 5.6 | 11 | 7.3 |
| 14 | 7.2 | 12 | 6.0 |
| 15 | 5.3 | 13 | 6.1 |
| 16 | 5.2 | 14 | 4.1 |
| 17 | 7.5 | 15 | 6.9 |
| 18 | 6.8 | 16 | 6.8 |
| 19 | no protein | 19 | no protein |

Example 5

Quantitative Determination of HMGA1

The purified antibody 21G6/18 was used to determine the quantity of HMGA1 in nuclear protein extracts from lymphocytes. The assay is a competitive ELISA based on the competition of the bond between HMGA1 in the solid phase and HMGA1 in solution, in the presence of a specific antibody for the antigen. The quantitative determination of the HMGA1 concentration is carried out titrating the samples against a standard line obtained using the purified HMGA1 protein (as described in Example 4).

The results of the competitive ELISA for determining the HMGA1 in nuclear protein extracts from lymphocytes are shown in Table 3.

In particular, in Tab. 3 with healthy subjects and affected subjects, the dosed samples of different individuals are indicated. The values indicated in the table confirm what already emerged from the results of example 4, that is low concentrations of HMGA1 are related to a pathological state of diabetes or insulin resistance. The values indicated in Table 3, expressed in µg/ml, refer to the concentrations of HMGA1 protein in the sample. In the column for healthy subjects, some samples (11, 12, 18, 20, 23, 24, 25, 29) deviate from the general trend according to which high concentrations of HMGA1 are characteristic of healthy subjects. The test confirms its reliability, understood as reproducibility and statistical significance. The P value is in fact lower than 0.05, and specifically $P<0.0015$. The data shown in Tab. 3 therefore confirm the high reliability of the test.

It is also possible to note, by analysing the values of the concentration of HMGA1 protein in the samples from affected subjects, how the detection limit of the protein concentration is particularly effective, being able to discriminate even very low concentration values and with a high sensitivity even in particularly close numerical ranges. The data confirm what already emerged from example 4, in which a value of 0.035 µg/ml is indicated as the detection limit of the concentration of HMGA1 in the assay.

TABLE 3

Determination of HMGA1 in biological samples

| HEALTHY SUBJECTS | | AFFECTED SUBJECTS | |
| --- | --- | --- | --- |
| sample | µg/ml | sample | µg/ml |
| 1 | 5.12 | 31 | 2.60 |
| 2 | 5.65 | 32 | 1.23 |
| 3 | 10.90 | 33 | 1.51 |
| 4 | 10.90 | 34 | 1.55 |
| 5 | 16.49 | 35 | 1.99 |
| 6 | 7.52 | 36 | 3.38 |
| 7 | 7.42 | 37 | 6.20 |
| 8 | 7.63 | 38 | 4.12 |
| 9 | 4.70 | 39 | 3.82 |
| 10 | 8.43 | 40 | 1.89 |
| 11 | 2.02 | 41 | 4.13 |
| 12 | 2.65 | 42 | 3.61 |
| 13 | 6.57 | 43 | 4.52 |
| 14 | 7.92 | 44 | 4.37 |
| 15 | 8.50 | 45 | 3.18 |
| 16 | 4.56 | 46 | 1.38 |
| 17 | 3.25 | 47 | 3.46 |
| 18 | 2.88 | 48 | 5.63 |
| 19 | 7.72 | 49 | 4.28 |
| 20 | 1.84 | 50 | 1.23 |
| 21 | 5.99 | 51 | 2.95 |
| 22 | 6.39 | 52 | 2.35 |
| 23 | 2.15 | 53 | 4.40 |
| 24 | 1.99 | 55 | 2.80 |
| 25 | 2.32 | 56 | 5.24 |
| 26 | 4.56 | 57 | 6.90 |
| 27 | 5.87 | 58 | 3.66 |
| 28 | 4.04 | 59 | 4.01 |
| 29 | 2.77 | 60 | 5.13 |
| 30 | 3.54 | | |

The invention claimed is:

1. Clone 2G16, Autoritá Internazionale di Deposito accession number PD 08001.

2. Clone 2G16/18, Autoritá Internazionale di Deposito accession number PD 08002.

3. Monoclonal antibody generated by clone 2G16, Autoritá Internazionale di Deposito accession number PD 08001 according to claim 1.

4. Monoclonal antibody generated by clone 2G16/18, Autoritá Internazionale di Deposito accession number PD 08002 according to claim 2.

5. A method for the quantitative determination of HMGA1 in biological fluids comprising incubating a biological fluid with the monoclonal antibody of claim 3.

6. A method for the quantitative determination of HMGA1 in biological fluids comprising incubating a biological fluid with the monoclonal antibody of claim 4.

7. Kit for the determination of HMGA1 comprising the monoclonal antibodies according to claim 3.

8. Kit for the determination of HMGA1 comprising the monoclonal antibodies according to claim 4.

* * * * *